US009983288B2

(12) United States Patent
Jin et al.

(10) Patent No.: US 9,983,288 B2
(45) Date of Patent: May 29, 2018

(54) **FREE-BREATHING MYOCARDIAL T2* MAPPING USING SINGLE-HEARTBEAT, MULTI-SHOT, GRADIENT ECHO-ECHO PLANAR IMAGING (GRE-EPI) AND AUTOMATIC NON-RIGID MOTION CORRECTION**

(71) Applicant: Ohio State Innovation Foundation, Columbus, OH (US)

(72) Inventors: Ning Jin, Powell, OH (US); Marie-Pierre Jolly, Hillsborough, NJ (US); Orlando Simonetti, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 665 days.

(21) Appl. No.: 14/604,898

(22) Filed: Jan. 26, 2015

(65) Prior Publication Data

US 2015/0309146 A1 Oct. 29, 2015

Related U.S. Application Data

(60) Provisional application No. 61/983,564, filed on Apr. 24, 2014.

(51) Int. Cl.
*G01R 33/50* (2006.01)
*G01R 33/565* (2006.01)
(Continued)

(52) U.S. Cl.
CPC ........ *G01R 33/56509* (2013.01); *A61B 5/055* (2013.01); *A61B 5/7207* (2013.01); *G01R 33/50* (2013.01); *G01R 33/5616* (2013.01)

(58) Field of Classification Search
CPC .............. G01R 33/56509; G01R 33/50; G01R 33/5616; A61B 5/055; A61B 5/7207
See application file for complete search history.

(56) References Cited

U.S. PATENT DOCUMENTS

2014/0113008 A1* 4/2014 Dharmakumar ..... A61B 5/0044 424/699
2015/0268320 A1* 9/2015 Akcakaya ............. G01R 33/50 324/309

(Continued)

OTHER PUBLICATIONS

Edelman, R et al (Fast Selective Black Blood Imaging), Radiology 1991, 181:655-660.*

(Continued)

*Primary Examiner* — Clayton E Laballe
*Assistant Examiner* — Ruifeng Pu
(74) *Attorney, Agent, or Firm* — Meunier Carlin & Curfman LLC

(57) ABSTRACT

A novel free-breathing myocardial T2* mapping combining multiple single-shot black-blood GRE-EPI images with automatic non-rigid motion correction. The present disclosure describes a method of accurate myocardial T2* measurements that is insensitive to respiratory motion, and is likely to reduce sensitivity to arrhythmia as well since each image is acquired in a single heart beat. The T2*-weighted GRE-EPI images are motion corrected using, e.g., automatic non-rigid motion correction to reduce mis-registration due to respiratory motion. A T2* map is calculated using the motion-corrected T2*-weighted images by fitting pixel intensities to a, e.g., two-parameter mono-exponential model.

18 Claims, 7 Drawing Sheets

(51) Int. Cl.

| | |
|---|---|
| ***A61B 5/055*** | (2006.01) |
| ***A61B 5/00*** | (2006.01) |
| *G01R 33/561* | (2006.01) |

(56) References Cited

U.S. PATENT DOCUMENTS

| | | | | |
|---|---|---|---|---|
| 2016/0078604 | A1* | 3/2016 | Guo ....................... | A61B 5/055 382/131 |
| 2016/0139225 | A1* | 5/2016 | Basha .................... | G01R 33/36 324/309 |
| 2016/0183815 | A1* | 6/2016 | Dharmakumar ..... | A61B 5/4848 424/450 |

OTHER PUBLICATIONS

Biglands, J, (Cardiovascular magnetic resonance physics for clinicians; part II), J. Cardiovascular Mag Res. 2012.*

Anderson, L. J. et al. (2001). Cardiovascular T 2-star(T 2*) magnetic resonance for the early diagnosis of myocardial iron overload. European Heart Journal, 22(23), 2171-2179.

Giri, S. et al. (2012). Myocardial T2 mapping with respiratory navigator and automatic nonrigid motion correction. Magnetic Resonance in Medicine, 68(5), 1570-1578.

He, T. et al. (2007). Black-blood T2* technique for myocardial iron measurement in thalassemia. Journal of Magnetic Resonance Imaging, 25(6), 1205-1209.

* cited by examiner

Figure 2:
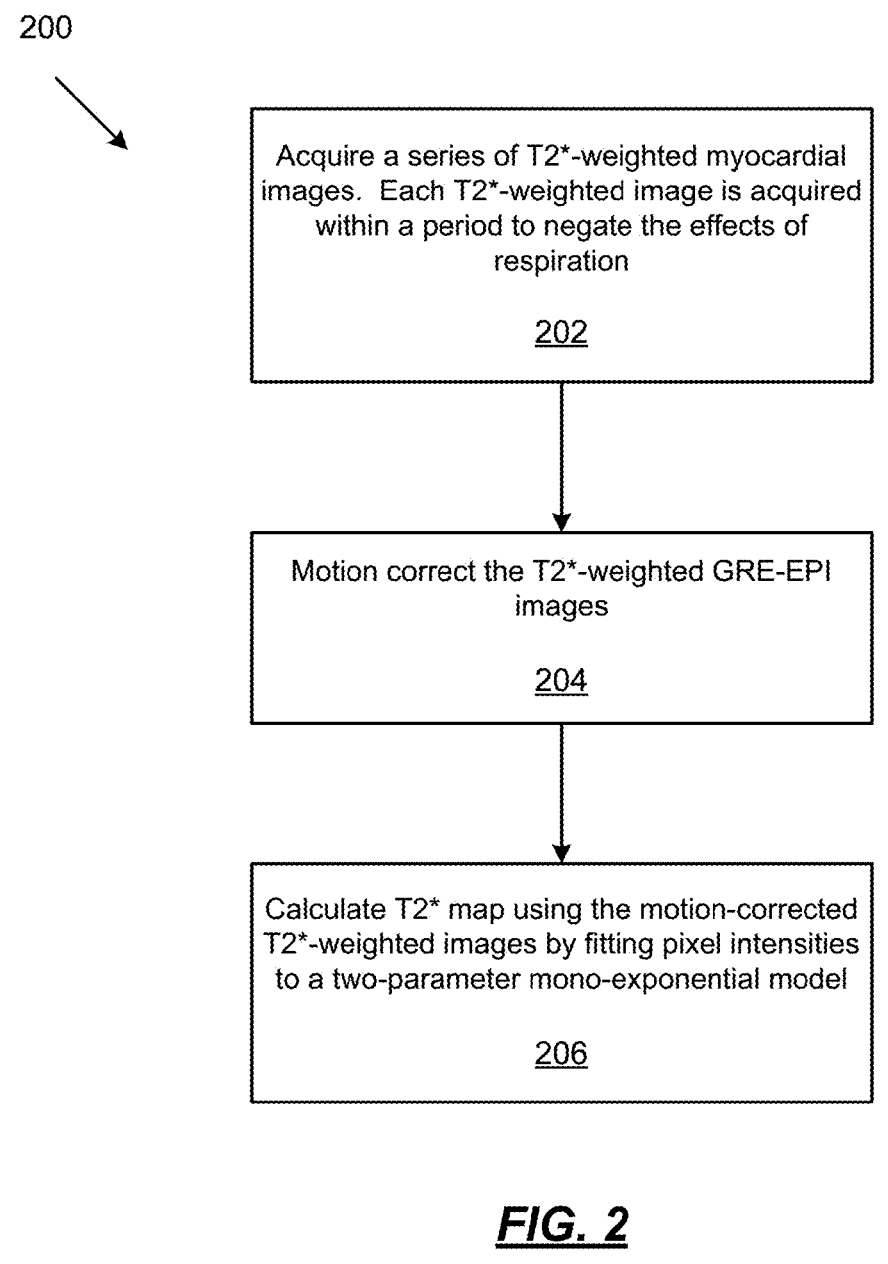

200

Acquire a series of T2*-weighted myocardial images. Each T2*-weighted image is acquired within a period to negate the effects of respiration

202

Motion correct the T2*-weighted GRE-EPI images

204

Calculate T2* map using the motion-corrected T2*-weighted images by fitting pixel intensities to a two-parameter mono-exponential model

FREE-BREATHING MYOCARDIAL T2* MAPPING USING SINGLE-HEARTBEAT, MULTI-SHOT, GRADIENT ECHO-ECHO PLANAR IMAGING (GRE-EPI) AND AUTOMATIC NON-RIGID MOTION CORRECTION

This application claims priority to U.S. Provisional Patent Application No. 61/983,564, filed Apr. 24, 2014, entitled "FREE-BREATHING MYOCARDIAL T2* MAPPING USING SINGLE-HEARTBEAT, MULTI-SHOT, GRADIENT ECHO—ECHO PLANAR IMAGING (GRE-EPI) AND AUTOMATIC NON-RIGID MOTION CORRECTION," the disclosure of which is incorporated herein by reference in its entirety.

BACKGROUND

Cardiac failure caused by myocardial iron overload is the most common cause of death in patients with thalassemia. Myocardial T2* mapping is widely used to detect and quantify myocardial iron in these patients. The conventional myocardial T2* mapping approach uses an ECG-triggered segmented black-blood multi-echo gradient echo (mGRE) sequence. As with any segmented k-space acquisition, data are acquired over multiple heart beats (e.g., 10 heart beats) and a patient breath-hold is required to avoid respiratory motion artifacts. However, this strategy fails in severely ill patients and others unable to breath-hold.

SUMMARY

Disclosed herein are systems and methods for myocardial T2* mapping using single-heartbeat, multi-shot, gradient-echo echo-planar imaging (GRE-EPI) coupled with automatic non-rigid motion correction. The proposed technique accurately quantifies T2* values in the heart with less sensitivity to respiratory motion than the standard, segmented k-space acquisition.

In accordance with an aspect of the invention, a method and MRI apparatus is disclosed that performs a method for performing free-breathing myocardial T2* mapping. The method may include acquiring a series of T2*-weighted myocardial images; motion correcting the T2*-weighted images; and calculating a T2* map.

In accordance with an aspect of the invention, a method for performing T2* image mapping is disclosed that includes using a single-shot, multi-echo, GRE-EPI sequence with different echo times to acquire a series of T2*-weighted images; applying motion correction to multiple measurements for each echo time to determine an average of the T2*-weighted images; applying motion correction to the averaged T2*-weighted images; and determining a T2* map using the averaged motion-corrected T2*-weighted images.

In accordance with an aspect of the invention, method for performing free-breathing myocardial T2* mapping is disclosed that includes using a single-shot, multi-echo, GRE-EPI sequence with different echo times to acquire a series of free-breathing myocardial T2*-weighted images, each of the T2*-weighted images being acquired in a single heart beat; applying motion correction to multiple measurements for each echo time to determine an average of the myocardial T2*-weighted images; applying motion correction to the averaged T2*-weighted images; and determining a T2* map using the averaged motion-corrected T2*-weighted images.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 2 is an example operational flow in accordance with the present disclosure;

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. While implementations will be described for remotely accessing applications, it will become evident to those skilled in the art that the implementations are not limited thereto, but are applicable for remotely accessing any type of data or service via a remote device.

Example Environment

Figure 1:
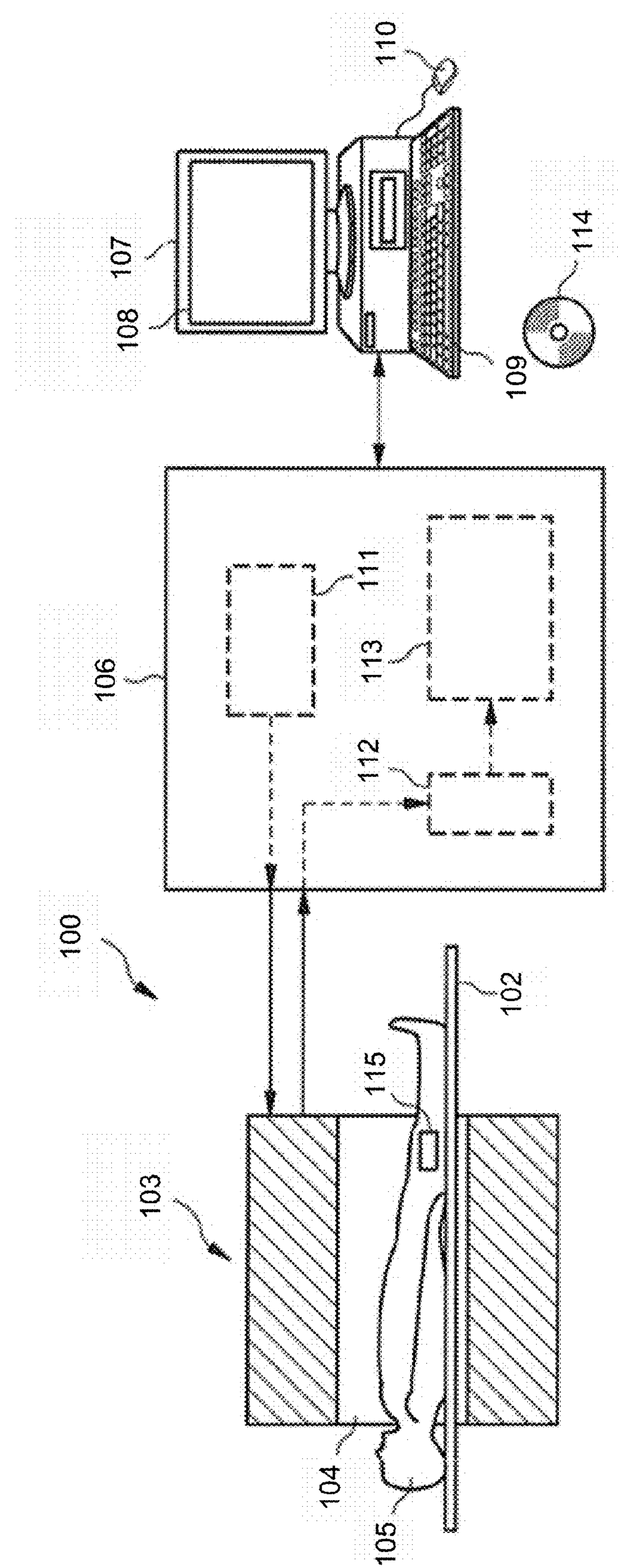
FIG. 1 is a diagram of a structure of a magnetic resonance imaging (MRI) apparatus according to an exemplary embodiment of the present invention.

FIG. 1 is a view illustrating a structure of an example magnetic resonance imaging (MRI) apparatus 100 that may be used to acquire image data. The MRI apparatus 100 includes a scanner 103 that generates magnetic fields used for the MR examination within a measurement space 104 having a patient table 102. A controller 106 includes an activation unit 111, a receiver device 112 and an evaluation module 113. During a phase-sensitive flow measurement, MR data are recorded by the receiver device 112, such that MR data are acquired in, e.g., a measurement volume or region 115 that is located inside the body of a patient 105.

An evaluation module 113 prepares the MR data such that they can be graphically presented on a monitor 108 of a computing device 107 and such that images can be displayed. In addition to the graphical presentation of the MR data, a three-dimensional volume segment to be measured can be identified by a user using the computing device 107. The computing device may include a keyboard 109 and a mouse 110.

Software for the controller 106 may be loaded into the controller 106 using the computing device 107. Such software may implement a method(s) to process data acquired by the MRI apparatus 100, as described below. It is also possible the computing device 107 to operate such software. Yet further, the software implementing the method(s) of the disclosure may be distributed on removable media 114 so that the software can be read from the removable media 14 by the computing device 107 and be copied either into the controller 106 or operated on the computing device 107 itself.

In an implementation, the data acquired by the MRI apparatus 100 of FIG. 1, may be processed as described below with reference to FIGS. 2-9.

Figure 3:
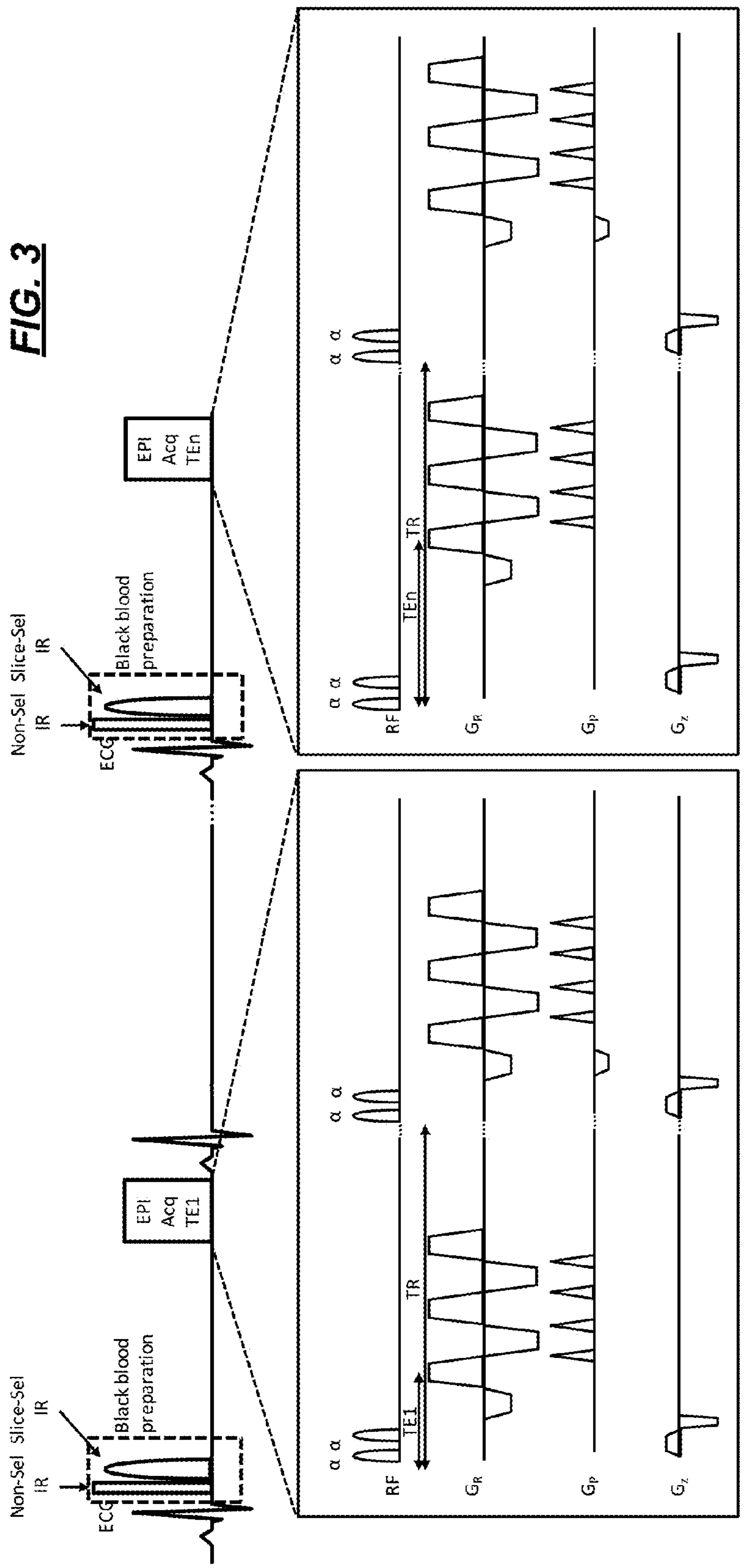
FIG. 3 illustrates an example pulse sequence timing diagram that illustrates the image acquisition in the operational flow of FIG. 2.

With reference to FIG. 2, there is illustrated an example operational flow 200 for free-breathing myocardial T2* mapping using single-heartbeat, multi-shot, GRE-EPI and automatic non-rigid motion correction. In accordance with aspects of the present disclosure, each image is acquired within a time period (e.g., less than 300 ms) that is short enough to negate the effects of motion caused by respiration of the patient under study. At 202, a series of T2*-weighted myocardial images are acquired. For example, each T2*-weighted image is acquired in a single heart beat such that for each single heartbeat, one single image is acquired. A pulse sequence strategy may be implemented to acquire the series of T2* weighted images using a single-heartbeat, multi-shot, black-blood GRE-EPI sequence at 8 different echo times (e.g., TE=1.2, 3, 5, 7, 9, 11, 13 and 14 ms) with a flip angle of 10°, a TR of 20 ms, an echo-train-length of 5, a sampling bandwidth of 1500 Hz/pixel, a slice thickness of 10 mm, a GRAPPA acceleration rate of 2 with 24 reference lines, a field-of-view (FOV) of 380 mm and a matrix=192×144. This yields a voxel size of 1.9×1.9×10 $mm^3$. Thus, the acquisition of images at 202 takes advantage of characteristics of multi-shot GRE-EPI, which provides for longer echo times (TE) and a fast single-heartbeat image, enabling the capability to acquire images in a single heartbeat with minimal sensitivity to respiratory and cardiac motion. FIG. 3 illustrates an example pulse sequence timing diagram that illustrates the image acquisition in step 202.

Figure 4:
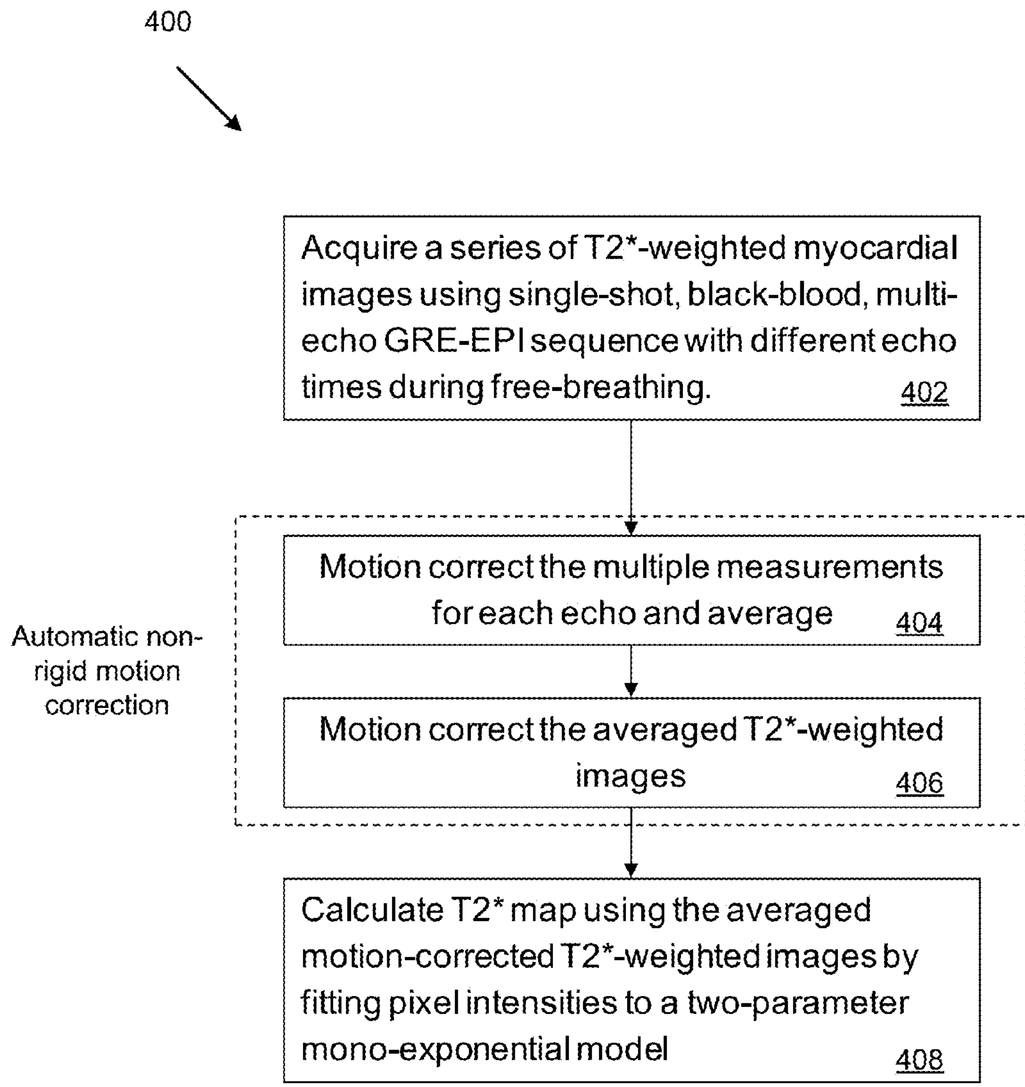
FIG. 4 another example operational flow in accordance with the present disclosure.
Figure 5:
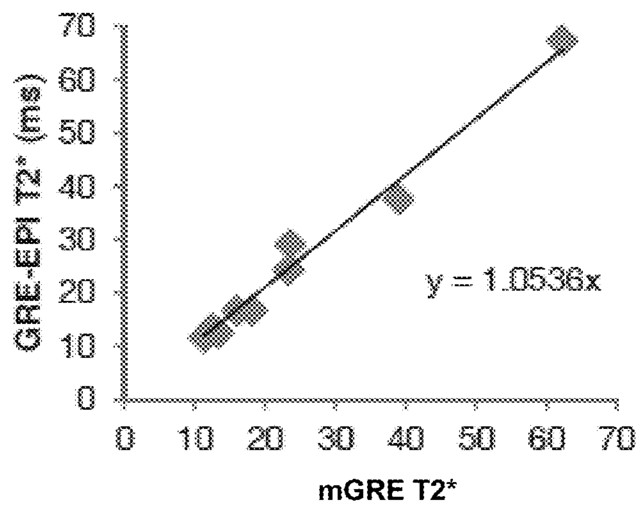
FIG. 5 is an example regression plot illustrating a strong correlation between the T2* measured using mGRE and GRE-EPI in phantoms over a wide range of T2* values.

Additionally or alternatively, the image acquisition at 202 may be performed using a single-shot EPI technique, where the T2* weighted images are acquired within the same heartbeat, as described with reference to FIG. 4.

A rapid binomial water-excitation pulse was used to suppress signal from fat tissue and minimize chemical displacement artifacts. For black-blood imaging, double inversion pulses (slice-selective and non-selective) were applied at the R-wave trigger and the inversion time was set to extend into diastole for effective nulling of blood signal. Each of the eight different echo time images was acquired in a single heart beat with an acquisition window of 280 ms; i.e., fast enough to avoid respiratory motion artifacts.

At 204, the T2*-weighted GRE-EPI images (each image acquired in a single-heartbeat) are motion corrected using automatic non-rigid motion correction to reduce mis-registration due to respiratory motion. At 206, a T2* map is calculated using the motion-corrected T2*-weighted images by fitting pixel intensities to a one-parameter, two-parameter or three-parameter mono-exponential model, a multi-exponential model, or other similar models. The T2* map may be a representation of a value of a quantitative parameter that is assigned to each pixel in the image.

Additionally or optionally, each of the T2*-weighted images could be repeated with multiple measurements to increase signal-noise-ratio (SNR) of the reconstructed T2* image. With reference to FIG. 4, there is illustrated another example operational flow 400 in accordance with the present disclosure, At 402, a series of free-breathing myocardial T2*-weighted images are acquired using a single-shot, multi-echo, GRE-EPI sequence with different echo times. At 402, Each T2*-weighted image is acquired in a single heart beat and repeated for multiple measurements. At 404, motion correction is applied to the multiple measurements for each echo and an average is determined. At 406, motion correction is applied to the averaged T2*-weighted images. At 408, a T2* map is determined using the averaged motion-corrected T2*-weighted images by fitting pixel intensities to a two-parameter mono-exponential model.

MRI

All imaging was performed using a 1.5 T MAGNETOM Avanto clinical scanner (Siemens Medical Solutions, Erlangen, Germany) with body matrix and spine coils for signal reception.

Phantom Studies

Nine T2* phantoms were constructed with Falcon tubes filled with water and doped with 0.25, 0.31, 0.5, 0.62, 0.75, 0.87, 1, 1.12, 1.25 mmol/L $MnCl_2$ to produce a wide range of T2* values. T2* measurements were performed using the proposed black-blood GRE-EPI sequence with a simulated heart rate of 60 beats/min and 16 signal averages. For comparison, T2* maps were also acquired using the standard ECG-triggered segmented black-blood mGRE sequence with 4 signal averages.

Patient Studies

Experiments were conducted in 72 patients referred for clinical cardiac MR cardiomyopathy evaluation. Myocardial T2* images were acquired in the short axis view using both the black-blood GRE-EPI sequence during free breathing, and the standard ECG-triggered segmented black-blood seg-mGRE sequence during one breath-hold (BH) of 14 heart beats.

Data Processing

In patient studies, T2*-weighted images from the GRE-EPI sequence were motion corrected using automatic non-rigid motion correction to reduce image mis-registration due to respiratory motion. No motion correction was performed for phantom images. T2* maps were calculated by fitting pixel intensities to a two-parameter mono-exponential model (Signal=MO*exp (−TE/T2*)). Regions-of-interest (ROIs) were drawn in the tubes in phantom images and in the interventricular septum and liver in patient images. The mean T2* values within the ROIs were calculated using both sequences and compared using a pair-wise t-test.

Results

Phantom studies: A strong correlation was observed between the T2* measured using GRE-EPI and the T2* measured using mGRE (r=0.992) (see, FIG. 5). No statistically significant difference was observed between the T2* values measured using the two methods (p=0.234).

Patient Studies

Figure 6:
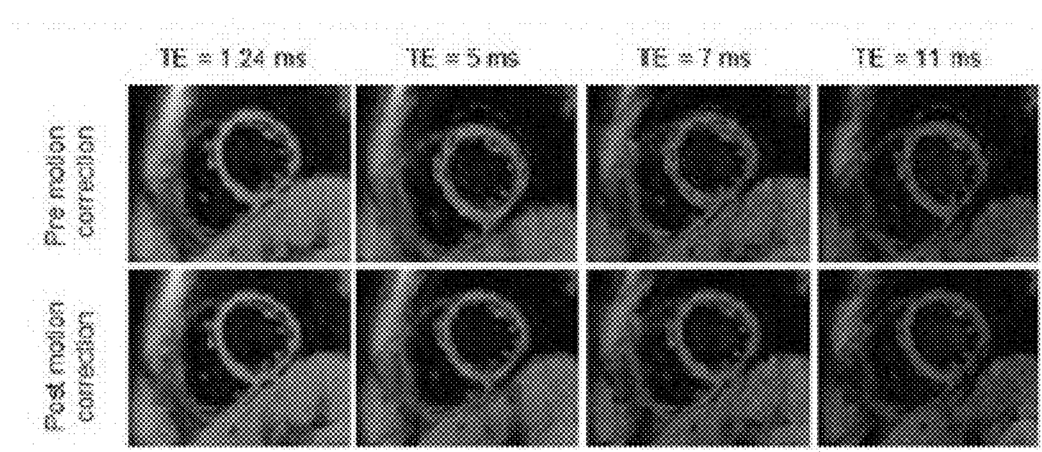
FIG. 6 illustrates example free-breathing images acquired with different echo times (TE), with and without motion correction.
Figure 7:
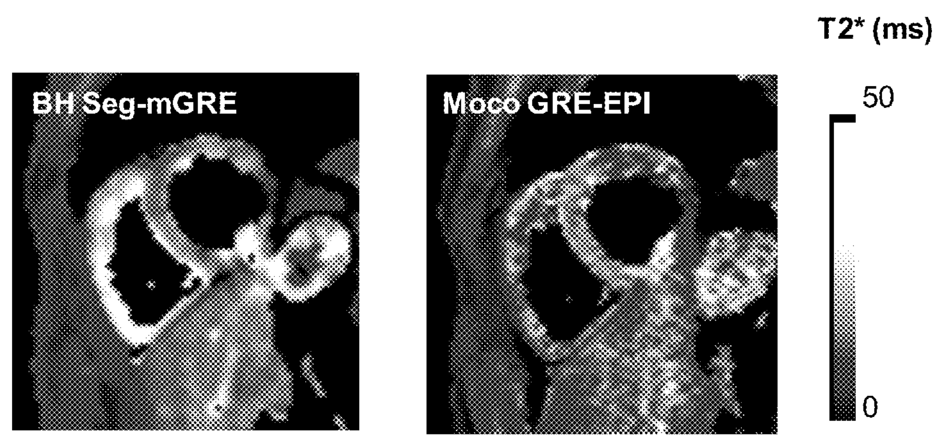
FIGS. 7-8 are representative myocardial T2* maps acquired using breath-hold mGRE (a) and free-breathing GRE-EPI with motion correction (b)
Figure 8:
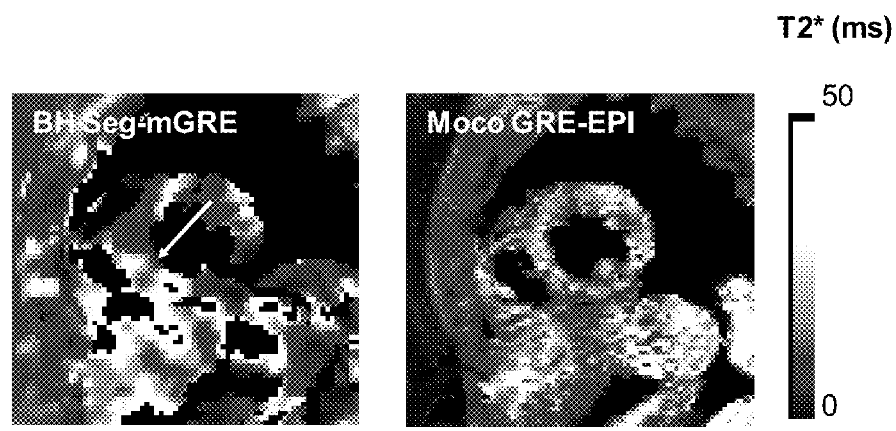
Figure 9:
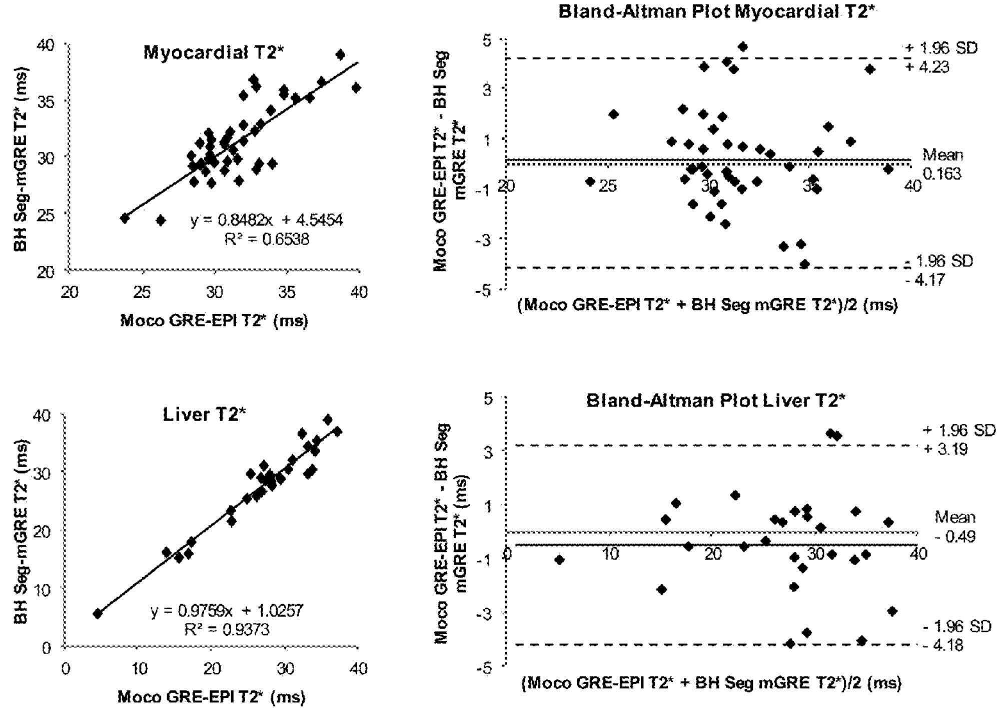
FIG. 9 illustrates a comparison between T2* measured in the intra-ventricular septum and the liver from the BH seg-mGRE techniques.

FIG. 6 shows example GRE-EPI source images and the effect of the automatic nonrigid motion correction on single-heartbeat, multi-shot GRE-EPI images acquired during free-breathing. GRE-EPI images at TE=1.24, 5, 7, 11 ms prior to motion correction (top row) and post motion correction (bottom row) are shown. Contours were drawn on the TE=1.24 ms image and projected onto the images acquired using longer TEs. The automatic non-rigid motion correction successfully reduced image mis-registration due to respiratory motion. FIG. 7 shows an example of "good" T2* map quality for BH seg-mGRE and moco GRE-EPI in a patient able to breath hold. FIG. 8 shows another example in patients unable to breath hold. Compared to the conventional T2* map from BH seg-mGRE, free-breathing moco GRE-EPI improves T2* map quality. As shown in FIG. 9, comparisons between T2* measured in the intra-ventricular septum and the liver from the BH seg-mGRE techniques in 45 patients with adequate images using both techniques demonstrated strong correlations (r=0.77 and 0.97) and no significant differences (p=0.78 and 0.24).

Thus, the present disclosure describes a novel method for free-breathing myocardial T2* mapping combining multiple single-heartbeat, multi-shot, black-blood GRE-EPI images with automatic non-rigid motion correction. The approach provides accurate myocardial T2* measurements and is insensitive to respiratory motion, and is likely to reduce sensitivity to arrhythmia as well since each image is acquired in a single heart beat. While image registration does not account for through-plane motion, the same approach of registering multiple images, each acquired in a single heartbeat, has proven successful for myocardial T1 and T2 mapping. Additionally, the acquisition could be combined with techniques such as navigator respiratory gating, or other methods to restrict data acquisition to a common phase of the respiratory cycle, and thereby avoid significant through-plane motion.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for performing free-breathing T2* image mapping, comprising:

acquiring a series of images with varying levels of T2*-weighting, the acquiring of individual images being performed within a predetermined time period having a length that substantially negates effects of motion caused by respiration;

motion correcting the T2*-weighted images; and calculating a T2* map, wherein the predetermined time period is approximately 300 ms.

2. The method of claim 1, further comprising using single-heartbeat, multi-shot, gradient-echo echo-planar imaging (GRE-EPI) to acquire the images.

3. The method of claim 1, further comprising motion correcting the T2*-weighted images using an automatic non-rigid motion correction to reduce mis-registration due to respiratory and/or cardiac motion.

4. The method of claim 1, further comprising calculating the T2* map by fitting pixel intensities to a model.

5. The method of claim 1, wherein the images are myocardial images.

6. The method of claim 5, wherein the predetermined time period is a single heartbeat.

7. A method for performing free-breathing T2* image mapping, comprising:

acquiring a series of images with varying levels of T2*-weighting, the acquiring of individual images being performed within a predetermined time period having a length that substantially negates effects of motion caused by respiration;

motion correcting the T2*-weighted images;

calculating a T2* map;

using a pulse sequence to acquire the series of images using a single-heartbeat, multi-shot, black-blood GRE-EPI sequence; and using different echo times (TE), wherein TE=1.2, 3, 5, 7, 9, 11, 13 and 14 ms.

8. The method of claim 7, further comprising using an acquisition window of 280 ms to acquire each of the series of images.

9. The method of claim 1, further comprising suppressing a signal from fat tissue and minimizing chemical displacement artifacts.

10. The method of claim 1, further comprising substantially nulling a blood signal.

11. A method for performing T2* image mapping, comprising:

using a single-shot, multi-echo, GRE-EPI sequence with different echo times to acquire a series of T2*-weighted images;

applying motion correction to multiple measurements for each echo time to determine an average weighting of the T2*-weighted images;

applying motion correction to the averaged T2*-weighted images; and determining a T2* map is determined using the averaged motion-corrected T2*-weighted images.

12. The method of claim 11, determining the T2* map by fitting pixel intensities to a two-parameter mono-exponential model.

13. The method of claim 11, wherein the T2*-weighted images are myocardial images.

14. The method of claim 13, further comprising:

acquiring each T2*-weighted image in a single heart beat; and repeating the acquiring for multiple measurements.

15. A method for performing free-breathing myocardial T2* mapping, comprising:

using a single-shot, multi-echo, GRE-EPI sequence with different echo times to acquire a series of free-breathing myocardial T2*-weighted images, each of the T2*-weighted images being acquired in a single heart beat;

applying motion correction to multiple measurements for each echo time to determine an average weighting of the myocardial T2*-weighted images;

applying motion correction to the averaged T2*-weighted images; and determining a T2* map is determined using the averaged motion-corrected T2*-weighted images.

16. The method of claim 15, determining the T2* map by fitting pixel intensities to a two-parameter mono-exponential model.

17. The method of claim 15, further comprising using different echo times (TE), wherein TE=1.2, 3, 5, 7, 9, 11, 13 and 14 ms.

18. The method of claim 17, further comprising using an acquisition window of 280 ms to acquire each of the series of myocardial T2*-weighted images.

* * * * *